US011224200B2

(12) United States Patent
Yoshinaga

(10) Patent No.: US 11,224,200 B2
(45) Date of Patent: Jan. 18, 2022

(54) EXCREMENT TREATMENT MATERIAL COMPRISING A NON-UNIFORM COATING AND METHOD FOR MANUFACTURING THE SAME

(71) Applicant: DAIKI CO., LTD., Tokyo (JP)

(72) Inventor: Junji Yoshinaga, Tokyo (JP)

(73) Assignee: DAIKI CO., LTD., Tokyo (JP)

( * ) Notice: Subject to any disclaimer, the term of this patent is extended or adjusted under 35 U.S.C. 154(b) by 316 days.

(21) Appl. No.: 16/506,034

(22) Filed: Jul. 9, 2019

(65) Prior Publication Data
US 2019/0327930 A1    Oct. 31, 2019

Related U.S. Application Data

(63) Continuation of application No. PCT/JP2018/005076, filed on Feb. 14, 2018.

(30) Foreign Application Priority Data

Mar. 24, 2017    (JP) .............................. JP2017-058791

(51) Int. Cl.
| | |
|---|---|
| *B32B 5/16* | (2006.01) |
| *A01K 1/01* | (2006.01) |
| *A01K 1/015* | (2006.01) |
| *B01J 2/00* | (2006.01) |
| *A61F 13/53* | (2006.01) |

(52) U.S. Cl.
CPC ............. *A01K 1/0155* (2013.01); *B01J 2/003* (2013.01); *A61F 2013/530992* (2013.01); *B01D 2253/20* (2013.01); *Y10T 428/2991* (2015.01)

(58) Field of Classification Search
CPC ......... Y10T 428/2438; Y10T 428/2495; Y10T 428/2991; A01K 1/0152; A01K 1/0154
USPC .................................................. 428/213, 403
See application file for complete search history.

(56) References Cited

U.S. PATENT DOCUMENTS

| | | | |
|---|---|---|---|
| 6,745,720 B2* | 6/2004 | Rasner ................. | A01K 1/0152 119/171 |
| 2012/0103270 A1* | 5/2012 | Greene ................. | A01K 1/0155 119/173 |

FOREIGN PATENT DOCUMENTS

JP        2003-219746 A        8/2003

* cited by examiner

*Primary Examiner* — Hoa (Holly) Le
(74) *Attorney, Agent, or Firm* — Oliff PLC

(57) ABSTRACT

An excrement treatment material includes a plurality of granules that absorb excrement. Each granule includes a granular core portion, and a coating portion. The core portion has a circular cross-section, and has a function of absorbing and retaining the excrement. The coating portion coats the core portion. The coating portion has a function of causing the plurality of granules, which have absorbed the excrement, to adhere to each other. In a cross-section of each granule that is in the same plane as the cross-section of the core portion, a thickness of the coating portion on one side of the core portion is smaller than a thickness of the coating portion on another side of the core portion.

18 Claims, 2 Drawing Sheets

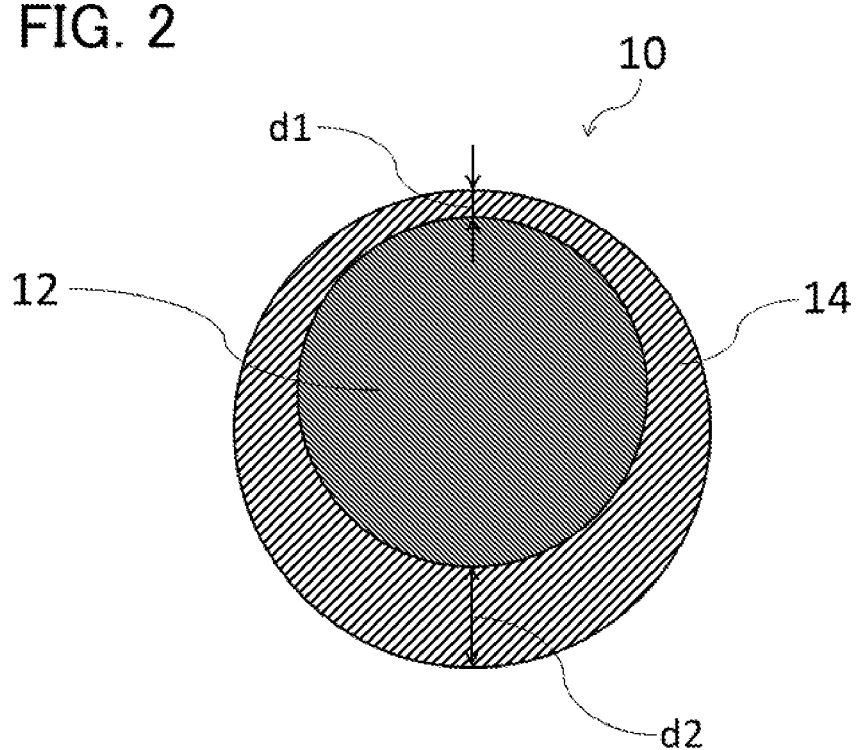

EXCREMENT TREATMENT MATERIAL COMPRISING A NON-UNIFORM COATING AND METHOD FOR MANUFACTURING THE SAME

CROSS REFERENCE TO RELATED APPLICATION

This is a Continuation of International Application No. PCT/JP2018/005076 filed Feb. 14, 2018, which claims the benefit of Japanese Application No. 2017-058791 filed Mar. 24, 2017. The contents of these applications are hereby incorporated by reference in their entirety.

TECHNICAL FIELD

The present invention relates to an excrement treatment material for absorbing excrement and a method for manufacturing the same.

BACKGROUND ART

Patent Document 1 describes a waste treatment material (excrement treatment material) that is used to treat excrement. The excrement treatment material described in this document is made of a plurality of water-absorbing granules. Each granule includes a granular core portion and a coating portion that coats the core portion. The core portion has a function of absorbing and retaining excrement. Furthermore, the coating portion has a function of causing the plurality of granules, which have absorbed the excrement, to adhere to each other. Accordingly, after the excrement treatment material is used, an aggregate of a plurality of granules that have absorbed excrement is formed.

CITATION LIST

Patent Document

Patent Document 1: JP 2003-219746A

SUMMARY OF INVENTION

Technical Problem

In this manner, the coating portion contributes to forming an aggregate of granules after use. However, on the other hand, the coating portion is provided so as to coat the core portion, and thus it prevents excrement from quickly reaching the core portion. This aspect decreases the water absorption of conventional excrement treatment materials.

Solution to Problem

The present invention was achieved in view of the aforementioned problem, and it is an object thereof to provide an excrement treatment material that can suppress a decrease in the water absorption due to the presence of coating portions, and a method for manufacturing the same.

The present invention is directed to an excrement treatment material including a plurality of granules that absorb excrement, wherein each of the granules includes: a granular core portion that has a circular cross-section and has a function of absorbing and retaining the excrement; and a coating portion that is provided so as to coat the core portion, and has a function of causing the plurality of granules, which have absorbed the excrement, to adhere to each other, and, in a cross-section of each of the granules that is in the same plane as the cross-section of the core portion, a thickness of the coating portion on one side of the core portion is smaller than a thickness of the coating portion on another side of the core portion.

In this excrement treatment material, the thickness of the coating portion on one side of the core portion is smaller than the thickness of the coating portion on the other side. If the thickness of a portion of the coating portion is small in this manner, excrement can quickly reach the core portion through this portion.

Also, the present invention is directed to a method for manufacturing an excrement treatment material including a plurality of granules that absorb excrement, including a granule forming step of forming the plurality of granules, wherein the granule forming step includes: a core portion forming step of forming granular core portions each having a circular cross-section and having a function of absorbing and retaining the excrement; and a coating portion forming step of forming coating portions so as to coat the core portions, the coating portions having a function of causing the plurality of granules, which have absorbed the excrement, to adhere to each other, and in the coating portion forming step, the coating portions are formed such that, in a cross-section of each of the granules that is in a same plane as the cross-section of the core portion, a thickness of the coating portion on one side of the core portion is smaller than a thickness of the coating portion on another side of the core portion.

In this manufacturing method, each coating portion is formed such that the thickness of the coating portion on one side of the core portion is smaller than the thickness of the coating portion on the other side. If the thickness of a portion of the coating portion is small in this manner, in the manufactured excrement treatment material, excrement can quickly reach the core portion through this portion.

Advantageous Effects of Invention

According to the present invention, it is possible to realize an excrement treatment material that can suppress a decrease in the water absorption due to the presence of coating portions, and a method for manufacturing the same.

BRIEF DESCRIPTION OF DRAWINGS

FIG. 2 is a cross-sectional view showing a granule 10.

DESCRIPTION OF EMBODIMENTS

Figure 1:
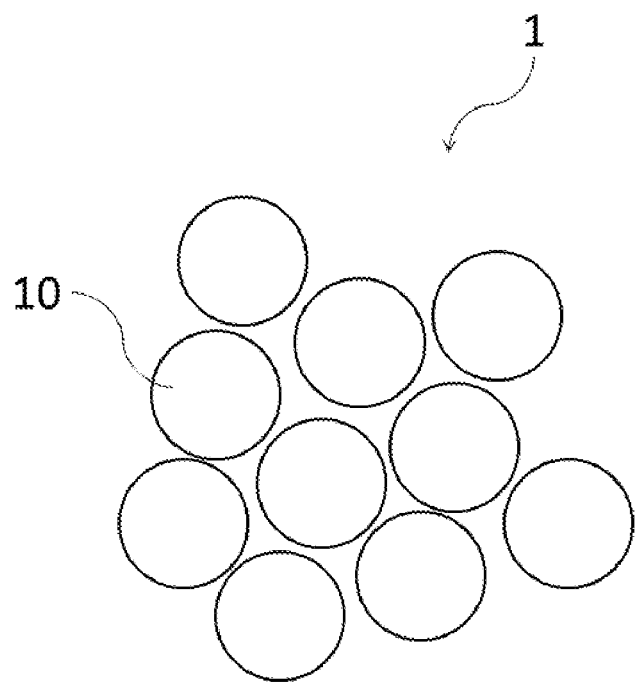
FIG. 1 is a schematic diagram showing an embodiment of an excrement treatment material according to the present invention.

Hereinafter, embodiments of the present invention will be described in detail with reference to the drawings. It should be noted that, in the description of the drawings, identical elements are denoted by the identical reference numerals, and redundant descriptions are omitted.

FIG. 1 is a schematic diagram showing an embodiment of an excrement treatment material according to the present invention. An excrement treatment material 1 is an excrement treatment material that absorbs human or animal excrement (feces and urine), and includes a plurality of granules 10.

The granules 10 are water-absorbing granules, and absorb excrement. A main material of the granules 10 is an organic substance. "Main material of the granules 10" as used herein means a material having the largest weight proportion among the materials of which the granules 10 are made. Examples of the organic substance include papers, used tea leaves, plastics, and bean curd lees.

"Papers" means materials containing pulp as the main component. Examples of the papers include classified products of wallpaper made of polyvinyl chloride (papers obtained by classifying wallpaper made of polyvinyl chloride), fluff pulp, paper-making sludge, and pulp sludge, in addition to ordinary paper. Examples of the plastics include classified products of a paper diaper (plastics obtained by classifying paper diapers). It is preferable that dried bean curd lees are used as the bean curd lees.

FIG. 2 is a cross-sectional view showing the granule 10. Each granule 10 includes a core portion 12 and a coating portion 14. The core portion 12 has a granular shape, and, as shown in this diagram, has a circular cross-section. Examples of the granular shape include a sphere, a circular cylinder, and an ellipsoid. The core portion 12 has a function of absorbing and retaining excrement. A main material of the core portion 12 is an organic substance.

The core portion 12 may or may not contain an adhesive material. Examples of the adhesive material include CMC (carboxymethyl cellulose), PVA (polyvinyl alcohol), dextrin, and water-absorbing polymers.

The coating portion 14 coats the core portion 12. The coating portion 14 coats the entire surface of the core portion 12. A main material of the coating portion 14 is also an organic substance. The coating portion 14 contains an adhesive material, and has a function of causing the plurality of granules 10, which have absorbed the excrement, to adhere to each other. In this embodiment, the coating portion 14 contains a water-absorbing polymer, as the adhesive material. The water-absorbing polymer contained in the coating portion 14 has an average particle size of preferably 20 μm or less, and more preferably 10 μm or less. "Average particle size" as used herein means the smallest mesh opening through which 50 wt % or more of particles can pass when a water absorbing polymer, which is a group of a large number of particles, is put through a sieve. Accordingly, "having an average particle size of 20 μm or less" means that, when a water-absorbing polymer is put through a sieve with 20-μm mesh openings, 50 wt % or more of the particles can pass therethrough.

In the cross-section of each granule 10 (cross-section shown in FIG. 2) that is in the same plane as the cross-section of the core portion 12, a thickness d1 of the coating portion 14 on one side (the upper side in the drawing) of the core portion 12 is smaller than a thickness d2 of the coating portion 14 on the other side (the lower side in the drawing) of the core portion 12. It is preferable that the thickness d1 is less than or equal to half of the thickness d2. For example, the thickness d1 is 0.5 mm or less, and the thickness d2 is 1 mm or more. It is preferable that the thickness of the coating portion 14 becomes gradually smaller from the other side toward the one side.

Then, an example of a method for manufacturing the excrement treatment material 1 will be described as an embodiment of a method for manufacturing the excrement treatment material according to the present invention. This manufacturing method includes a granule forming step of forming a plurality of granules 10. The granule forming step includes a core portion forming step and a coating portion forming step.

The core portion forming step is a step of forming core portions 12. In this step, a plurality of core portions 12 are formed by granulating a core portion material (a material for forming the core portions 12) using a granulator. Examples of the granulator include an extrusion granulator. Before the granulation, the core portion material is subjected to pretreatment such as pulverization, kneading, or adding water, as necessary.

The coating portion forming step is a step of forming coating portions 14 so as to coat the core portions 12. In order to form the coating portions 14, it is sufficient to attach a powdery coating material (a material for forming the coating portions 14) to the surface of the core portions 12. The coating material can be attached to the surface, for example, through sprinkling or spraying. At that time, the amount of coating material that is to be attached to one side of the core portion 12 is made smaller, so that the thickness d1 of the coating portion 14 on the one side is smaller than the thickness d2 of the coating portion 14 on the other side. Subsequently, aftertreatment such as sieving (sizing) or drying is performed as necessary. Accordingly, the excrement treatment material 1 including the plurality of granules 10 is obtained.

Hereinafter, effects of this embodiment will be described. In this embodiment, each coating portion 14 is formed such that the thickness d1 of the coating portion 14 on one side of the core portion 12 is smaller than the thickness d2 of the coating portion 14 on the other side. If the thickness of a portion of the coating portion 14 (a portion on one side of the core portion 12) is small in this manner, excrement can quickly reach the core portion 12 through this portion. Accordingly, it is possible to realize an excrement treatment material 1 that can suppress a decrease in the water absorption due to the presence of coating portions 14, and a method for manufacturing the same.

Furthermore, since the thickness of another portion (portion on the other side of the core portion 12) of the coating portion 14 is large, the volume of the entire coating portion 14 can be sufficiently ensured. Accordingly, a large quantity of coating portions 14 can contribute to forming an aggregate. This aspect is advantageous for improving the aggregating strength of granules 10 that have absorbed excrement.

If the core portions 12 do not contain an adhesive material, only the coating portions 14 contribute to forming an aggregate of the granules 10. Accordingly, in this case, it is particularly important to cause a large quantity of coating portions 14 to contribute to forming an aggregate.

In order to obtain an excrement treatment material 1 that is excellent in terms of both the water-absorbing performance and the aggregating strength in this manner, a larger difference between the thickness d1 and the thickness d2 is more advantageous. From this point of view, it is preferable that the thickness d1 is less than or equal to half of the thickness d2. Furthermore, it is preferable that the thickness d1 is 0.5 mm or less, and the thickness d2 is 1 mm or more.

If the thickness of each coating portion 14 becomes gradually smaller from the other side toward the one side of the core portion 12, the coating portion 14 can be formed, for example, by spraying the coating material onto the core portion 12 mainly from one direction (the above-described other side). This method is advantageous in that the coating portion 14 in which the thickness d1 on the one side of the core portion 12 is smaller than the thickness d2 on the other side can be formed with ease.

Each granule 10 has a two-layered structure consisting of the core portion 12 and the coating portion 14. Accordingly, functions can be shared such that the core portion 12 mainly has a function of absorbing and retaining water and the coating portion 14 mainly has a function of forming an aggregate. The plurality of functions can be together improved by selecting materials of the core portion 12 and the coating portion 14 so as to be suitable for the respective functions.

The main material of the granules 10 is an organic substance. Accordingly, it is possible to obtain granules 10 suitable for incineration. If the granules 10 are suitable for incineration in this manner, the excrement treatment material 1 after use can be disposed of as burnable garbage, and the convenience for users can be improved. Note that it is not essential that the main material of the granules 10 is an organic substance.

The granules 10 after use have to be disposed of. If the granules 10 are flushable in flush toilets, the convenience for users can be further improved. In order to make the granules 10 flushable in flush toilets, it is necessary that the granules 10 have sufficient water solubility (properties in which fibers or particles that are bonded to each other quickly separate and disperse in water, upon coming into contact with water).

Regarding this aspect, conventional excrement treatment materials are problematic in that, since core portions are coated by coating portions, not only the water absorption but also the water solubility decreases. The reason for this is that the coating portions prevent water of flush toilets from reaching the core portions. In this embodiment, as described above, the thickness of a portion of each coating portion 14 is small, and thus a decrease in the water solubility can be also suppressed.

The coating portions 14 contain a water-absorbing polymer, as the adhesive material. If the coating portions contain a water-absorbing polymer in this manner, the problem that the water solubility of the conventional excrement treatment material decreases becomes apparent. The reason for this is that, since a water-absorbing polymer swells when absorbing liquid, the coating portions further prevent water of flush toilets from reaching the core portions when the water-absorbing polymer swells. Accordingly, in this case, the excrement treatment material 1 that can suppress a decrease in the water solubility is particularly useful. Note that it is not essential that the coating portions 14 contains a water-absorbing polymer.

Swelling of the water-absorbing polymer when it absorbs liquid is suppressed through pulverization into fine particles. Accordingly, in order to suppress swelling of the water-absorbing polymer in the coating portions 14 to the extent possible, an average particle size of the water-absorbing polymer contained in the coating portions 14 is preferably 20 μm or less, and more preferably 10 μm or less.

LIST OF REFERENCE NUMERALS

1 Excrement treatment material
10 Granule
12 Core portion
14 Coating portion

The invention claimed is:

1. An excrement treatment material comprising a plurality of granules that absorb excrement,
wherein each of the granules includes:
a granular core portion that has a circular cross-section and has a function of absorbing and retaining the excrement; and
a coating portion that is provided so as to coat the core portion, and has a function of causing the plurality of granules, which have absorbed the excrement, to adhere to each other, and
in a cross-section of each of the granules that is in the same plane as the cross-section of the core portion, a thickness of the coating portion on one side of the core portion is smaller than a thickness of the coating portion on another side of the core portion.

2. The excrement treatment material according to claim 1, wherein the thickness of the coating portion on the one side is less than or equal to half of the thickness of the coating portion on the other side.

3. The excrement treatment material according to claim 2, wherein the thickness of the coating portion on the one side is 0.5 mm or less, and
the thickness of the coating portion on the other side is 1 mm or more.

4. The excrement treatment material according to claim 1, wherein the thickness of the coating portion becomes gradually smaller from the other side toward the one side.

5. The excrement treatment material according to claim 1, wherein a main material of each of the granules is an organic substance.

6. The excrement treatment material according to claim 1, wherein the core portion does not contain an adhesive material.

7. The excrement treatment material according to claim 1, wherein the coating portion contains a water-absorbing polymer.

8. The excrement treatment material according to claim 7, wherein the water-absorbing polymer has an average particle size of 20 μm or less.

9. The excrement treatment material according to claim 8, wherein the water-absorbing polymer has an average particle size of 10 μm or less.

10. A method for manufacturing an excrement treatment material including a plurality of granules that absorb excrement, comprising a granule forming step of forming the plurality of granules,
wherein the granule forming step includes:
a core portion forming step of forming granular core portions each having a circular cross-section and having a function of absorbing and retaining the excrement; and
a coating portion forming step of forming coating portions so as to coat the core portions, the coating portions having a function of causing the plurality of granules, which have absorbed the excrement, to adhere to each other, and
in the coating portion forming step, the coating portions are formed such that, in a cross-section of each of the granules that is in a same plane as the cross-section of the core portion, a thickness of the coating portion on one side of the core portion is smaller than a thickness of the coating portion on another side of the core portion.

11. The method for manufacturing an excrement treatment material according to claim 10,
wherein, in the coating portion forming step, the coating portions are formed such that the thickness of the coating portion on the one side is less than or equal to half of the thickness of the coating portion on the other side.

12. The method for manufacturing an excrement treatment material according to claim 11,
wherein, in the coating portion forming step, the coating portions are formed such that the thickness of the coating portion on the one side is 0.5 mm or less and the thickness of the coating portion on the other side is 1 mm or more.

13. The method for manufacturing an excrement treatment material according to claim 10,
   wherein, in the coating portion forming step, the coating portions are formed such that the thickness of the coating portion becomes gradually smaller from the other side toward the one side.

14. The method for manufacturing an excrement treatment material according to claim 10,
   wherein, in the granule forming step, the plurality of granules whose main material is an organic substance are formed.

15. The method for manufacturing an excrement treatment material according to claim 10,
   wherein, in the core portion forming step, the core portions containing no adhesive material are formed.

16. The method for manufacturing an excrement treatment material according to claim 10,
   wherein, in the coating portion forming step, the coating portions containing a water-absorbing polymer are formed.

17. The method for manufacturing an excrement treatment material according to claim 16,
   wherein the water-absorbing polymer has an average particle size of 20 μm or less.

18. The method for manufacturing an excrement treatment material according to claim 17,
   wherein the water-absorbing polymer has an average particle size of 10 μm or less.

\* \* \* \* \*